(12) United States Patent
Kim et al.

(10) Patent No.: US 10,981,155 B2
(45) Date of Patent: Apr. 20, 2021

(54) CATALYST SYSTEM FOR OLEFIN OLIGOMERIZATION AND METHOD FOR PREPARING OLEFIN OLIGOMER USING SAME

(71) Applicant: LOTTE CHEMICAL CORPORATION, Seoul (KR)

(72) Inventors: Hee Young Kim, Daejeon (KR); Min Jae Shin, Daejeon (KR); Tae Jin Kim, Daejeon (KR); Seung Woong Yoon, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 27 days.

(21) Appl. No.: 16/335,146

(22) PCT Filed: Sep. 14, 2017

(86) PCT No.: PCT/KR2017/010105
§ 371 (c)(1),
(2) Date: Mar. 20, 2019

(87) PCT Pub. No.: WO2018/056644
PCT Pub. Date: Mar. 29, 2018

(65) Prior Publication Data
US 2019/0275507 A1 Sep. 12, 2019

(30) Foreign Application Priority Data

Sep. 21, 2016 (KR) .................. 10-2016-0120689
Sep. 21, 2016 (KR) .................. 10-2016-0120691

(51) Int. Cl.
| | | |
|---|---|---|
| *B01J 31/18* | (2006.01) | |
| *B01J 31/14* | (2006.01) | |
| *C07C 2/34* | (2006.01) | |
| *B01J 23/26* | (2006.01) | |
| *C07C 2/32* | (2006.01) | |
| *C07F 5/06* | (2006.01) | |
| *B01J 31/22* | (2006.01) | |
| *B01J 31/12* | (2006.01) | |

(52) U.S. Cl.
CPC ............. *B01J 31/182* (2013.01); *B01J 23/26* (2013.01); *B01J 31/143* (2013.01); *C07C 2/32* (2013.01); *C07C 2/34* (2013.01); *C07F 5/066* (2013.01); *B01J 31/122* (2013.01); *B01J 31/2234* (2013.01); *B01J 2231/20* (2013.01); *B01J 2531/004* (2013.01); *B01J 2531/007* (2013.01); *B01J 2531/0205* (2013.01); *B01J 2531/31* (2013.01); *B01J 2531/62* (2013.01); *C07C 2531/14* (2013.01); *C07C 2531/22* (2013.01)

(58) Field of Classification Search
CPC ........ B01J 31/182; B01J 23/26; B01J 31/143; B01J 31/2234; B01J 31/122; B01J 2231/20; B01J 2531/004; B01J 2531/007; B01J 2531/0205; B01J 2531/31; B01J 2531/62; C07C 2/32; C07C 2/34; C07C 2531/14; C07C 2531/22; C07F 5/066
See application file for complete search history.

(56) References Cited

U.S. PATENT DOCUMENTS

| | | | |
|---|---|---|---|
| 5,376,612 A | 12/1994 | Reagen et al. | |
| 5,563,312 A | 10/1996 | Knudsen et al. | |
| 2017/0217854 A1 | 8/2017 | Lee et al. | |
| 2018/0071725 A1* | 3/2018 | Klosin | ............... C07F 9/6568 |

FOREIGN PATENT DOCUMENTS

| | | |
|---|---|---|
| KR | 2012-0112590 A | 10/2012 |
| KR | 2015-0002549 A | 1/2015 |
| KR | 2015-0037581 A | 4/2015 |
| KR | 2016-0062525 A | 6/2016 |
| KR | 2016-0064840 A | 6/2016 |
| WO | 2015/133805 A1 | 9/2015 |

OTHER PUBLICATIONS

International Search Report issued in International Application No. PCT/KR2017/010105 dated Dec. 22, 2017 (2 pages).
Written Opinion issued in International Application No. PCT/KR2017/010105 dated Dec. 22, 2017 (5 pages).

* cited by examiner

*Primary Examiner* — Ali Z Fadhel
(74) *Attorney, Agent, or Firm* — Osha Bergman Watanabe & Burton LLP

(57) ABSTRACT

Disclosed are a novel catalyst system which is a catalyst system for selectively oligomerizing olefin including ethylene and may trimerize and tetramerize olefin, different from the catalyst system for olefin oligomerization reported until now, and a method for preparing an olefin oligomer using same. The present invention provides a catalyst system for olefin oligomerization, including a ligand compound represented by Formula 1; a chromium compound; and a metal alkyl compound, and a method for preparing an olefin oligomer using same.

14 Claims, No Drawings

CATALYST SYSTEM FOR OLEFIN OLIGOMERIZATION AND METHOD FOR PREPARING OLEFIN OLIGOMER USING SAME

TECHNICAL FIELD

The present invention relates to a catalyst system for olefin oligomerization and a method for preparing olefin oligomer using same, and more particularly, to a novel catalyst system by which trimerization and tetramerization of olefin are possible, and a method for preparing olefin oligomer using same.

BACKGROUND ART

Linear alpha-olefins are important materials used in a comonomer, a cleansing agent, a lubricant, a plasticizer, etc., and are commercially widely used, and particularly, 1-hexene and 1-octene are used a lot as comonomers for controlling the density of polyethylene during preparing linear low-density polyethylene (LLDPE).

Particularly, in the preparation process of LLDPE known before, copolymerization of ethylene with a comonomer such as an alpha-olefin including 1-hexene and 1-octene was performed to control density by forming branches at a polymer backbone. Accordingly, in preparing LLDPE having the high comonomer content, the price of the comonomer is a large part of the manufacturing cost. Therefore, various attempts have been conducted for reducing the unit cost for preparing the comonomer. In addition, since the alpha-olefin has different application field and market size depending on the kind thereof, technique for selectively producing a specific alpha-olefin is commercially very important. Recently, research on chrome catalyst technique for preparing 1-hexene, 1-octene, etc. with high selectivity through selective ethylene oligomerization, is conducted a lot.

For example, Philips Co. disclosed in 1994 (see U.S. Pat. No. 5,376,612) an ethylene trimerization catalyst system with high activity and high selectivity, using a trivalent chromium compound, a pyrrole compound and non-hydrolyzed aluminum alkyl, as a catalyst system for polymerizing olefin such as ethylene to prepare 1-hexene, etc., and after that, based on the catalyst system, 1-hexene has been commercially produced from 2003. A catalyst system using tris(2-ethylhexanoate) chromium(III) ($Cr(EH)_3$, $EH=O2C8H15$) among various trivalent chromium compounds, showed particularly excellent catalyst activity, and a catalyst system using $Cr(EH)_3$ has been intensively studied and commercialized.

Such a catalyst system using $Cr(EH)_3$ may be prepared by, for example, in an unsaturated hydrocarbon solvent by injecting a mixture solution of triethylaluminum and ethylaluminum dichloride to an unsaturated hydrocarbon solvent (toluene, etc.) in which $Cr(EH)_3$ and 2,5-dimethylpyrrole are mixed. Usually, the trimerization reaction of olefin is performed in a saturated hydrocarbon solvent such as cyclohexane, and it is required that the unsaturated hydrocarbon solvent of the catalyst system thus prepared is removed under a reduced pressure in vacuum and the catalyst system is dissolved again in a saturated hydrocarbon solvent such as cyclohexane and used, or the catalyst system prepared in an unsaturated hydrocarbon solution phase is used for trimerization reaction and the unsaturated hydrocarbon solvent used for preparing a catalyst is separated and removed after finishing the reaction. In addition, during preparing a catalyst using $Cr(EH)_3$, black precipitate is formed as by-products while forming a catalyst activating species and requires a removing process using a filter (see U.S. Pat. No. 5,563,312). Such a removing process of an unsaturated hydrocarbon solvent such as toluene, a filtering process, etc. may act as a burden during commercialization. If the catalyst system is prepared in an aliphatic hydrocarbon solvent such as cyclohexane, in which trimerization reaction is performed to omit the removing process of the unsaturated hydrocarbon solvent, the thermal stability of the catalyst thus prepared is degraded, and accordingly, a catalyst may be deactivated during trimerization reaction or catalyst selectivity may be degraded, and a large amount of by-products other than olefin trimer may be produced (see U.S. Pat. No. 5,563,312). Therefore, in the catalyst system of Phillips Co. etc., unsaturated hydrocarbon is included as an essential component.

Accordingly, International Laid-open Patent No. WO2015/133805 disclosed a raw material compound of a catalyst system in which by-products are not produced during preparing a catalyst, a filtering process is not necessary, and the preparation of a catalyst system in a saturated hydrocarbon solvent is possible, and a catalyst system having excellent catalyst activity during olefin polymerization (trimerization).

However, all prior art patents have limitations of selectively performing only trimerization in an olefin oligomerization process.

DISCLOSURE OF THE INVENTION

Technical Problem

The present invention provides a novel catalyst system which may trimerize and tetramerize olefin as a catalyst system capable of selectively oligomerizing olefin including ethylene, different from an olefin oligomerizing catalyst system reported until now, and a method for preparing an olefin oligomer using same.

Technical Solution

In order to solve the tasks, there is provided in the present invention a catalyst system for olefin oligomerization, including a ligand compound represented by the following Formula 1; a chromium compound; and a metal alkyl compound:

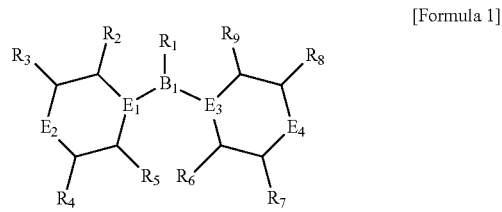

[Formula 1]

(in Formula 1, E1 and E3 are boron (B), carbon (C), nitrogen (N), silicon (Si) or phosphor (P), E2 and E4 are boron (B), carbon (C), nitrogen (N), oxygen (O), silicon (Si), phosphor (P) or sulfur (S), cases where both E1 and E2 are carbon (C) and both E3 and E4 are carbon, are excluded, B1 is an aluminum (Al), boron (B), nitrogen (N) or phosphor (P) element, R1 to R9 are each independently hydrogen, an alkyl group of 1 to 20 carbon atoms, a cycloalkyl group of 3 to 20 carbon atoms, an alkylsilyl group of 1 to 20 carbon atoms, a haloalkyl group of 1 to 20 carbon atoms, an aryl group of 6 to 40 carbon atoms, an arylalkyl group of 7 to 20 carbon atoms, an arylsilyl group of 6 to 20 carbon atoms, an alkylaryl group of 7 to 20 carbon atoms, an aryloxy group of 6 to 20 carbon atoms, a halogen group or an amino group.)

In addition, a catalyst system characterized in that, in Formula 1, E1 is nitrogen (N) and E2 is oxygen (O), or E3 is nitrogen (N) and E4 is oxygen (O), is provided.

In addition, a catalyst system characterized in that, the chromium compound is a compound containing chromium (III) or chromium(II), is provided.

In addition, a catalyst system characterized in that, the metal alkyl compound is one or more selected from the group consisting of an alkylaluminum compound, an alkylboron compound, an alkylmagnesium compound, an alkylzinc compound and an alkyllithium compound, is provided.

In addition, a catalyst system characterized in that, a molar ratio of the ligand compound, the chromium compound and the metal alkyl compound is 0.5:1:1 to 10:1:10,000 based on the chromium compound, is provided.

In addition, a catalyst system characterized in that, the olefin oligomerization includes trimerization and tetramerization, is provided.

In addition, there is provided a method for preparing an olefin oligomer, including a step of performing multimerization reaction of olefin in the presence of the catalyst system for olefin oligomerization.

In addition, a method characterized in that, a reaction of the olefin oligomerization is performed by homogeneous liquid phase reaction, is provided.

In addition, a method characterized in that, the reaction of olefin oligomerization is performed in an inert solvent which does not react with a compound in the catalyst system, is provided.

In addition, a method characterized in that, the reaction of the olefin oligomerization is performed at a temperature of 0 to 250° C. and a pressure of 1 to 200 bar, is provided.

Advantageous Effects

The present invention may provide a novel catalyst system which is capable of selectively trimerizing and tetramerizing olefin including ethylene by applying a compound which was not conventionally employed as a ligand compound in a catalyst system for olefin oligomerization, and may provide a method for preparing 1-hexene and 1-octene with excellent activity and selectivity using same.

MODE FOR CARRYING OUT THE INVENTION

Hereinafter, the present invention will be described in detail with reference to preferred embodiments. In explaining the present invention, if particular explanation on relevant prior art is considered to obscure the gist of the present invention, detailed explanation thereof will be omitted. Throughout the disclosure, if a part is referred to "include" a constituent element, the part does not exclude other constituent elements but may further include other constituent elements unless otherwise described.

The present invention discloses a catalyst system for olefin oligomerization, including a ligand compound; a chromium compound; and a metal alkyl compound.

The catalyst system for olefin oligomerization according to the present invention is used in a method for oligomerizing olefin, including a step of performing multimerizing reaction of olefin in the presence of the catalyst system.

According to the present invention, olefin including ethylene may be selectively trimerized and tetramerized.

Hereinafter, the catalyst system for olefin oligomerization according to a particular embodiment of the present invention will be explained in detail.

In the present invention, the ligand compound is a compound represented by the following Formula 1:

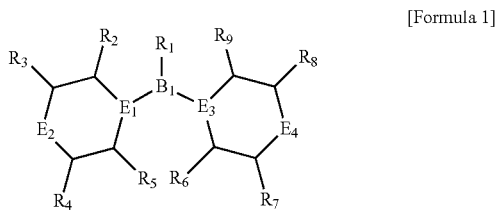

[Formula 1]

In Formula 1, E1 and E3 are boron (B), carbon (C), nitrogen (N), silicon (Si) or phosphor (P), E2 and E4 are boron (B), carbon (C), nitrogen (N), oxygen (O), silicon (Si), phosphor (P) or sulfur (S), cases where both E1 and E2 are carbon (C) and both E3 and E4 are carbon, are excluded. Preferably, E1 is nitrogen (N) and E2 is oxygen (O), or E3 is nitrogen (N) and E4 is oxygen (O).

In addition, B1 may be an aluminum (Al), boron (B), nitrogen (N) or phosphor (P) element, preferably, aluminum (Al).

R1 to R9 are each independently hydrogen, an alkyl group of 1 to 20 carbon atoms, a cycloalkyl group of 3 to 20 carbon atoms, an alkylsilyl group of 1 to 20 carbon atoms, a haloalkyl group of 1 to 20 carbon atoms, an aryl group of 6 to 40 carbon atoms, an arylalkyl group of 7 to 20 carbon atoms, an arylsilyl group of 6 to 20 carbon atoms, an alkylaryl group of 7 to 20 carbon atoms, an aryloxy group of 6 to 20 carbon atoms, a halogen group or an amino group. Here, the aryl group may be an aromatic hydrocarbon functional group such as phenyl, biphenyl, triphenyl, triphenylene, naphthalenyl, anthracenyl, phenalenyl, phenanthrenyl, fluorenyl, pyrenyl, chrysenyl, perylenyl, and azulenyl, an aromatic heterocyclic functional group such as dibenzothiophenyl, dibenzofuranyl, dibenzoselenophenyl, furanyl, thiophenyl, benzofuranyl, benzothiophenyl, benzoselenophenyl, carbazonyl, indolocarbazolyl, pyridylindolinine, pyrrolodipyridinyl, pyrazolyl, imidazolyl, triazolyl, oxazolyl, thiazolyl, oxadiazolinyl, oxatriazolyl, dioxazolyl, thiadiazolyl, pyridyl, pyridazinyl, pyrimidyl, pyrazinyl, triazinyl, oxazinyl, oxathiazinyl, oxadiazinyl, indolinine, benzimidazolyl, indazolyl, indoxazinyl, benzoxazolyl, benzisoxazolyl, benzothiazolyl, quinolinine, isoquinolinyl, cinnolinyl, quinazolyl, quinoxalinine, naphthyridyl, phthalazinyl, pteridinyl, xanthenyl, acridyl, phenazinyl, phenothiazinyl, phenoxazinyl, benzofuropyridyl, furodipyridyl, benzothienopyridyl, thienodipyridyl benzoselenophenopyridyl, and selenophenodipyridyl, or the like.

R1 to R9 in Formula 1 are more preferably hydrogen, an alkyl group of 1 to 20 carbon atoms, a cycloalkyl group or an aryl group in consideration of the stabilization of a central metal.

The term "olefin oligomerization" used in the present invention means oligomerization of olefin. According to the olefin number polymerized, olefin oligomerization is referred to trimerization, or tetramerization, and is commonly referred to multimerization. Particularly, in the present invention, the olefin oligomerization means selective preparation of 1-hexene and 1-octene from ethylene.

In addition, the "catalyst system" may refer to an optional composition, compound or complex, comprehensively, which shows catalyst activity with respect to "olefin oligomerization", irrespective of a simple mixture composition state of a ligand compound, a chromium compound and a metal alkyl compound, or reacting to form a separate catalytically active species, and includes the compounds or the reaction product thereof as a catalytically active species.

In addition, the selective olefin oligomerization reaction is closely related to a catalyst system used. The catalyst system used during the reaction of olefin oligomerization includes a chromium compound which acts as a main catalyst, and a metal alkyl compound which is a co-catalyst. In this case, the structure of the active catalyst may be changed according to the chemical structure of the ligand, and thus, the selectivity and activity of the olefin may change.

The inventor of the present invention found through experiments that a catalyst system for olefin oligomerization, including a ligand compound having a specific structure, a chromium compound and a metal alkyl compound as a co-catalyst, may easily control electronic, steric environment around a transition metal by suitably controlling the ligand compound, and the oligomerization of olefin, particularly, trimerization and tetramerization, with high catalyst activity and selectivity is possible, and completed the present invention.

Particularly, the ligand compound is a hexagonal ring compound, and in the hexagonal ring or a functional group connected with the hexagonal ring, one or more heteroatoms such as boron (B), nitrogen (N), oxygen (O), silicon (Si), phosphor (P) and sulfur (S) are included. Due to the structural characteristics, the ligand compound may be applied to a catalyst system for olefin oligomerization and show high oligomerization reaction activity, particularly, high selectivity with respect to 1-hexene and 1-octene. This is supposed to be obtained by the interaction between adjacent chromium active points.

In the present invention, the chromium compound acts as a main catalyst and preferably uses a compound containing chromium(III) or chromium(II) to increase reaction activity.

The chromium(III) compound may use chromium carboxylates, chromium naphthenates, chromium halides, chromium dionates, etc., and more particular examples may include chromium(III) 2,2,6,6-tetramethylheptanedionate, chromium(III) 2-ethylhexanoate, chromium(III) tris(2-ethylhexanoate), chromium(III) naphthenate [Cr(NP)3], bis(2-ethylhexanoate) chromium(III) hydroxide, bis(2-butanoate) chromium(III) hydroxide, chromium(III) chloride, chromic bromide, chromic fluoride, chromium(III) acetylacetonate, chromium(III) acetate, chromium(III) butyrate, chromium(III) neopentanoate, chromium(III) laurate, chromium(III) stearate, chromium(III) oxalate, bis(2-ethylhexanoate) chromium(III) hydroxide, etc.

In addition, particular examples of the chromium(II) compound may include chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate, etc.

Meanwhile, the chromium compound may be a solution state dissolved in a hydrocarbon solvent. The hydrocarbon solvent is an inert solvent which does not react with the chromium compound, the co-catalyst, etc., and may include benzene, benzene, toluene, heptane, cyclohexane, methylcyclohexane, methylcyclopentane, hexane, pentane, butane, isobutene, etc., without limitation.

In the catalyst system for olefin oligomerization of an embodiment, it is preferable that chromium(III) 2-ethylhexanoate, chromium(III) acetylacetonate or bis(2-ethylhexanoate) chromium(III) hydroxide is used as the chromium compound, and the chromium compound is dissolved in anhydrous toluene, an anhydrous cyclohexane solvent in consideration of the improvement of catalyst activity due to the solubility difference of the solvent.

In the present invention, the metal alkyl compound is the co-catalyst of the catalyst system for olefin oligomerization and may be any compounds as long as being used for multimerizing olefin in the presence of a common transition metal compound catalyst, without specific limitation. For example, the metal alkyl compound may use an alkylaluminum compound, an alkylboron compound, an alkylmagnesium compound, an alkylzinc compound, an alkyllithium compound, etc.

However, in order to show high selectivity and activity in the reaction of olefin oligomerization, the alkylaluminum compound may be used as the co-catalyst compound, and particular examples of such alkylaluminum compound may include triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, etc., and preferably, triethylaluminum, ethylaluminum dichloride, and ethylaluminum sesquichloride may be mixed and used. This case is preferable, because humidity may be effectively removed, and an electron donating atom is included to improve catalyst activity.

In the catalyst system for olefin oligomerization according to the present invention, the molar ratio of the ligand compound:chromium compound:metal alkyl compound may be 0.5:1:1 to 10:1:10,000, preferably, 0.5:1:100 to 5:1:3,000, to increase the selectivity with respect to linear alpha-olefin and dimerization reaction activity. However, the present invention is not limited thereto.

In the catalyst system for olefin oligomerization, including the ligand compound, the chromium compound and the metal alkyl compound, the three components or the precursors thereof may be added together at the same time or one by one order to an optionally suitable solvent in the presence or absence of a monomer to obtain a catalyst having activity. As the suitable solvent, heptane, toluene, cyclohexane, methylcyclohexane, 1-hexene, diethyl ether, tetrahydrofuran, acetonitrile, dichloromethane, chloroform, chlorobenzene, methanol, acetone, etc. may be used.

A method for preparing an olefin oligomer, including a step of performing multimerization reaction of olefin in the presence of the catalyst system for olefin oligomerization is provided. By using the catalyst system for olefin oligomerization according to the present invention, a method for oligomerizing olefin having improved reaction activity may be provided. In this case, the olefin may preferably be ethylene.

In the present invention, the olefin oligomerization may be a homogeneous liquid phase reaction in the presence or absence of an inert solvent using the catalyst system for olefin oligomerization, and a common apparatus and contact technique, a slurry reaction in which a portion or the entire of the catalyst system is undissolved, two-phase liquid/liquid reaction, bulk phase reaction in which an olefin product acts as a main medium, or gas phase reaction, preferably, homogeneous liquid phase reaction.

The olefin oligomerization reaction may be performed in an optional inert solvent which does not react with a catalyst compound and an activator. Suitable inert solvent includes benzene, toluene, xylene, cumene, heptane, cyclohexane, methylcyclohexane, methylcyclopentane, hexane, pentane, butane, isobutane, etc., without limitation. In this case, the solvent may be used after treating with a small amount of alkylaluminum to remove a small amount of water or air, which acts as a catalyst poison.

The olefin oligomerization reaction may be performed at a temperature of 0 to 250° C., preferably, 20 to 200° C., more preferably, 40 to 130° C. Too low reaction temperature may produce excessively large amount of undesired insoluble products such as a polymer, and too high reaction temperature may induce the decomposition of the catalyst system and a reaction product. Accordingly, the reaction is preferably performed at the above-mentioned temperature range. In addition, the olefin oligomerization reaction may be performed at a pressure of 1 to 200 bar, preferably, at a pressure of 10 to 150 bar. Too low reaction pressure may induce low catalyst activity. In addition, in order to promote the reaction in the preparation process of olefin oligomerization or increase the activity of the catalyst system, hydrogen may be added at 0.01 to 50 bars, preferably, 0.5 to 10 bars to a reactor.

Hereinafter, the present invention will be explained in more detail referring to Examples.

Preparation Example 1: Preparation of Ligand Compound

Under an inert atmosphere (nitrogen), in a two-neck flask, 2,6-dimethylmorpholine (30 mmol) was dissolved in toluene (60 mL), and the temperature was decreased to 0° C. using ice while stirring. If the temperature was sufficiently decreased, n-butyllithium (66 mmol, 2.5M in hexane, Aldrich reagent) was slowly added dropwisely for 10 minutes. After finishing the dropwise addition, the temperature was kept to 0° C. for 1 hour, and the ice of the reaction solution was removed to elevate the temperature to room temperature. The reaction was carried out while stirring for 12 hours, and after finishing the reaction, a toluene solvent was removed under a reduced pressure, and the white solid thus prepared was washed with dehydrated hexane (20 mL) twice. The white solid thus washed was dried under a reduced pressure and redissolved in toluene (60 mL). The temperature of the reaction solution was decreased to −78° C. using dry ice and ethylaluminum dichloride (15 mmol, 25 wt % in toluene, Aldrich reagent) was slowly added dropwisely for 10 minutes. Stirring was performed at the same temperature for 1 hour, and the temperature was elevated to room temperature, and then, the reaction was performed for 12 hours. After finishing the reaction, the white solid thus produced was filtered, and a toluene solvent was removed under a reduced pressure. The yellow oil thus obtained was redissolved in toluene (4 mL), and recrystallized at −3° C. to prepare a ligand compound represented by Formula 2 below:

[Formula 2]

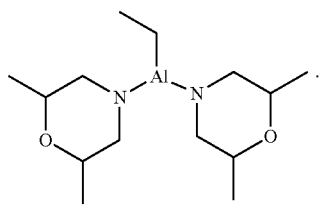

EXAMPLES: PREPARATION OF CATALYST SYSTEMS

Example 1

A typical catalyst system was prepared using chromium (III) 2-ethylhexanoate (21.3 mmol), ligand compound prepared by the preparation example 1 (63.8 mmol), ethylaluminum dichloride (85.1 mmol) and triethylaluminum (319 mmol) under an inert atmosphere (nitrogen). Particularly, chromium(III) 2-ethylhexanoate was dissolved in 30 ml of anhydrous toluene, and a ligand was added thereto. In a separate vessel, ethylaluminum dichloride and triethylaluminum were mixed together. Then, the aluminum alkyl solution was slowly poured into a chromium/ligand solution. After stirring the reaction solution for 5 minutes, solvents were removed under vacuum. The remaining oily liquid was diluted with 150 ml of cyclohexane, and the solution thus obtained was filtered to remove black precipitation from a filtrate containing a catalyst system. The resultant filtrate was diluted in toluene to a volume of 250 ml to prepare a final catalyst system.

Example 2

A catalyst system was prepared by the same method described in Example 1 except for using chromium(III) acetylacetonate instead of chromium(III) 2-ethylhexanoate in Example 1.

Example 3

A catalyst system was prepared by the same method described in Example 1 except for using bis(2-ethylhexanote) chromium(III) hydroxide instead of chromium(III) 2-ethylhexanoate in Example 1.

Comparative Example

A typical catalyst system was prepared using chromium (III) 2-ethylhexanoate (21.3 mmol), 2,5-dimethylpyrrole (63.8 mmol), ethylaluminum dichloride (85.1 mmol) and triethylaluminum (319 mmol) under an inert atmosphere (nitrogen). Particularly, chromium(III) 2-ethylhexanoate was dissolved in 30 ml of anhydrous toluene, and a ligand was added thereto. In a separate vessel, ethylaluminum dichloride and triethylaluminum were mixed together. Then, the aluminum alkyl solution was slowly poured into a chromium/ligand solution. After stirring the reaction solution for 5 minutes, solvents were removed under vacuum. The remaining oily liquid was diluted with 150 ml of cyclohexane, and the solution thus obtained was filtered to remove black precipitation from a filtrate containing a catalyst system. The resultant filtrate was diluted in toluene to a volume of 250 ml to prepare a final catalyst system.

Experimental Example

A 2 L stainless steel reactor was charged with nitrogen, 1 L cyclohexane was applied thereto, 3 ml of triethylaluminum was added thereto, and the reactor was charged with ethylene to 10 bars, followed by elevating the temperature to 90° C. Each of the catalyst solutions (30 μmol) thus prepared was injected into the reactor and the reactor was charged with ethylene to 35 bars, followed by stirring at a stirring speed of 500 rpm. After an hour, the supplying of ethylene to the reactor was stopped and the reactor was cooled to below 10° C. The excessive amount of ethylene in the reactor was discharged, and ethanol mixed with 10 vol % of hydrochloric acid was injected into a liquid contained in the reactor. A small amount of an organic layer sample was passed through a silica gel phase and dried, and then was analyzed by GC-FID. The remaining organic layer was filtered to separate a solid wax/polymer product. The solid product was dried in an oven at 80° C. for 8 hours, and weighed to obtain polyethylene. The results are listed in Table 1 below.

TABLE 1

| Division | 1-hexene (wt %) | 1-octene (wt %) | Activity (Kg of product/ mmol of cat) | PE (wt %) |
|---|---|---|---|---|
| Example 1 | 42.4 | 48.4 | 3.1 | 9.2 |
| Example 2 | 45.5 | 51.3 | 5.1 | 3.2 |
| Example 3 | 42.1 | 54.4 | 13.2 | 3.5 |
| Comparative Example | 99.3 | 0 | 3.1 | 0.7 |

As shown in Table 1, as a result of performing ethylene oligomerization reaction using the catalyst system of the present invention, it may be confirmed that 1-hexene and 1-octene were prepared at the same time with a high selectivity of 90 wt % or more, preferably, 95 wt % or more, and in case where a specific ligand compound and a chromium compound were used in combination (Examples 2 and 3), better activity was achieved when compared with the prior art (Comparative Example).

Preferred embodiments of the present invention have been explained in detail as above. The explanation of the present invention is only for illustration, and it should be understood that a person skilled in the art could easily change the inventive concept of the present invention into other preferred types without changing the technical spirit or essential feature of the present invention.

Accordingly, it should be interpreted that the scope of the present invention is represented by appended claims rather than the detailed description, and all changes or modifications derived from the meaning, range and equivalent concept of claims are included in the scope of the present invention.

The invention claimed is:

1. A catalyst system for olefin oligomerization, the catalyst system comprising:
   a ligand compound represented by the following Formula 1;
   a chromium compound; and
   a metal alkyl compound:

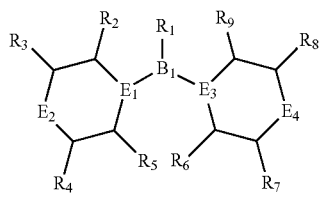

[Formula 1]

wherein in Formula 1, E1 and E3 are boron (B), carbon (C), nitrogen (N), silicon (Si) or phosphor (P), E2 and E4 are boron (B), nitrogen (N), oxygen (O), silicon (Si), phosphor (P) or sulfur (S), B1 is an aluminum (Al), boron (B), nitrogen (N) or phosphor (P) element, R1 to R9 are each independently hydrogen, an alkyl group of 1 to 20 carbon atoms, a cycloalkyl group of 3 to 20 carbon atoms, an alkylsilyl group of 1 to 20 carbon atoms, a haloalkyl group of 1 to 20 carbon atoms, an aryl group of 6 to 40 carbon atoms, an arylalkyl group of 7 to 20 carbon atoms, an arylsilyl group of 6 to 20 carbon atoms, an alkylaryl group of 7 to 20 carbon atoms, an aryloxy group of 6 to 20 carbon atoms, a halogen group or an amino group.

2. The catalyst system according to claim 1, wherein in Formula 1, E1 is nitrogen (N) and E2 is oxygen (O), or E3 is nitrogen (N) and E4 is oxygen (O).

3. The catalyst system according to claim 1, wherein the chromium compound is a compound containing chromium (III) or chromium(II).

4. The catalyst system according to claim 1, wherein the metal alkyl compound is one or more selected from the group consisting of an alkylaluminum compound, an alkylboron compound, an alkylmagnesium compound, an alkylzinc compound and an alkyllithium compound.

5. The catalyst system according to claim 1, wherein a molar ratio of the ligand compound, the chromium compound and the metal alkyl compound is 0.5:1:1 to 10:1:10,000 based on the chromium compound.

6. A method for preparing an olefin oligomer, the method comprising a step of performing multimerization reaction of olefin in the presence of the catalyst system for olefin oligomerization according to claim 1.

7. The method according to claim 6, wherein the multimerization comprises trimerization and tetramerization.

8. The method according to claim 6, wherein the multimerization is performed by homogeneous liquid phase reaction.

9. The method according to claim 6, wherein the multimerization is performed in an inert solvent which does not react with the compounds in the catalyst system.

10. The method according to claim 6, wherein the multimerization is performed at a temperature of 0 to 250° C. and a pressure of 1 to 200 bar.

11. A catalyst system for olefin oligomerization, the catalyst system comprising:
    a ligand compound represented by the following Formula 1;
    a chromium compound; and
    a metal alkyl compound:

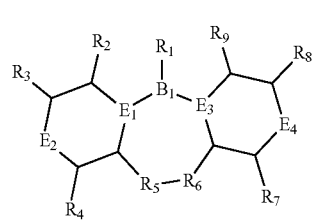

[Formula 1]

in Formula 1, E1 and E3 are nitrogen (N), E2 and E4 are oxygen (O), B1 is an aluminum (Al), boron (B), nitrogen (N) or phosphor (P) element, R1 to R9 are each independently hydrogen, an alkyl group of 1 to 20 carbon atoms, a cycloalkyl group of 3 to 20 carbon atoms, an alkylsilyl group of 1 to 20 carbon atoms, a haloalkyl group of 1 to 20 carbon atoms, an aryl group of 6 to 40 carbon atoms, an arylalkyl group of 7 to 20 carbon atoms, an arylsilyl group of 6 to 20 carbon atoms, an alkylaryl group of 7 to 20 carbon atoms, an aryloxy group of 6 to 20 carbon atoms, a halogen group or an amino group.

12. The catalyst system according to claim 11, wherein the chromium compound is a compound containing chromium (III) or chromium(II).

13. The catalyst system according to claim 11, wherein the metal alkyl compound is one or more selected from the group consisting of an alkylaluminum compound, an alkylboron compound, an alkylmagnesium compound, an alkylzinc compound and an alkyllithium compound.

14. The catalyst system according to claim 11, wherein a molar ratio of the ligand compound, the chromium compound and the metal alkyl compound is 0.5:1:1 to 10:1:10,000 based on the chromium compound.

* * * * *